United States Patent
Hwang et al.

(10) Patent No.: US 11,459,555 B2
(45) Date of Patent: Oct. 4, 2022

(54) METHOD OF PURIFYING NATIVE UBIQUITIN

(71) Applicant: POSTECH Research and Business Development Foundation, Pohang-si (KR)

(72) Inventors: Cheol-Sang Hwang, Pohang-si (KR); The Kha Nguyen, Pohang-si (KR); Da-Som Kim, Pohang-si (KR)

(73) Assignee: POSTECH RESEARCH AND BUSINESS DEVELOPMENT FOUNDATION, Pohang-Si (KR)

( * ) Notice: Subject to any disclaimer, the term of this patent is extended or adjusted under 35 U.S.C. 154(b) by 22 days.

(21) Appl. No.: 17/128,550

(22) Filed: Dec. 21, 2020

(65) Prior Publication Data
US 2021/0198651 A1 Jul. 1, 2021

(30) Foreign Application Priority Data

Dec. 31, 2019 (KR) .......................... 10-2019-0179913

(51) Int. Cl.
*C12N 9/00* (2006.01)
(52) U.S. Cl.
CPC ...................................... *C12N 9/93* (2013.01)
(58) Field of Classification Search
CPC ........ C12N 9/93; C12N 9/64; C07K 2319/21; C07K 14/47; C07K 2319/20; C07K 14/4702
See application file for complete search history.

(56) References Cited

PUBLICATIONS

Dong et al., Structure 19:1053-1063, 2011.*
The Agilent Technologies BL21(DE3) Competent Cells, BL21(DE3) pLysS Competent Cells, and BL21 Competent Cells Instruction Manual, pp. 1-11, 2010.*
Catanzariti et al., Protein Science 13:1331-1339, 2004.*
GE Healthcare Life Sciences Instruction 28-9920-17 AC, pp. 1-6, Apr. 2001.*
A L Haas et al., "The large scale purification of ubiquitin from human erythrocytes", Prep Biochem. 1985;15(1-2):49-60. doi: 10.1080/00327488508062433.
Keehyun Sung et al., "Development of Purification Process of Recombinant Human Vascular Endothelial Growth Factor (VEGF) using Fusion Protein", Korean Chem. Eng. Res., 55(3), 369-378 (2017).
KIPO, Office Action of KR 10-2019-0179913 dated Jun. 18, 2021.

* cited by examiner

*Primary Examiner* — Delia M Ramirez
(74) *Attorney, Agent, or Firm* — Lex IP Meister, PLLC

(57) ABSTRACT

The present invention relates to a method of purifying native ubiquitin without acid or heat treatment. The method presented here is designed to overcome limitations of acid or heat based ubiquitin purification in two different points of view. First, it decreases a chance of mixing other proteins resistant to acids or heat. Second, it includes no harsh condition, which might denature the ubiquitin. As a result, the purification of native ubiquitin becomes possible. The ubiquitin obtained herein is expected to be used for various purposes in technical fields.

9 Claims, 3 Drawing Sheets

Specification includes a Sequence Listing.

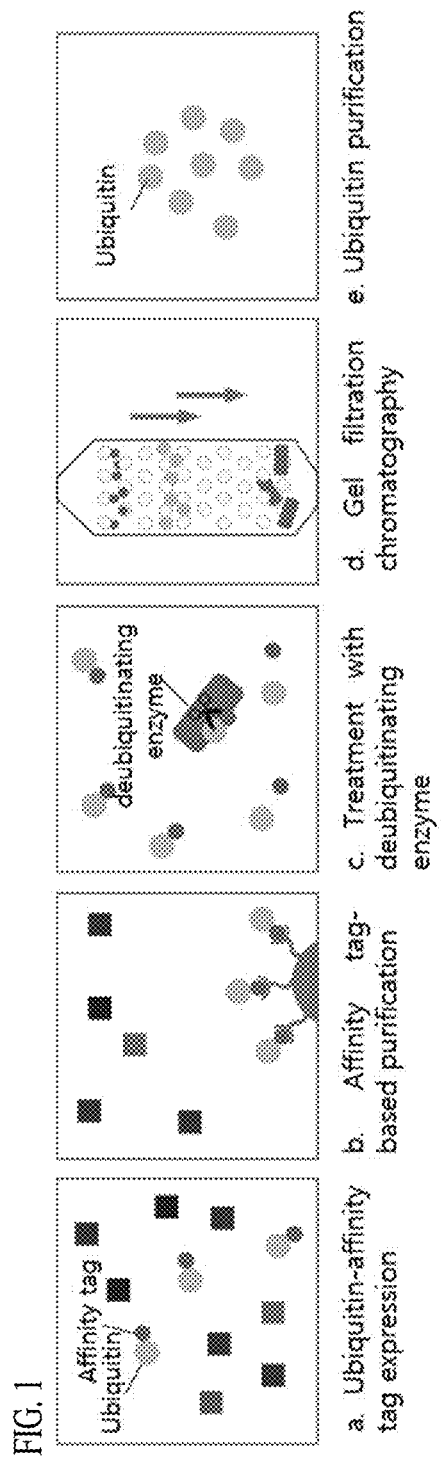

SEQUENCE LISTING

<160> NUMBER OF SEQ ID NOS: 1

<210> SEQ ID NO 1
<211> LENGTH: 3818
<212> TYPE: DNA
<213> ORGANISM: Artificial Sequence
<220> FEATURE:
<223> OTHER INFORMATION: pET23a-Ub-His6 vector

<400> SEQUENCE: 1

```
atccggatat agttcctcct ttcagcaaaa aaccctcaa gacccgttta gaggccccaa      60
ggggttatgc tagttattgc tcagcggtgg cagcagccaa ctcagcttcc tttcgggctt    120
tgttagcagc cggatctcag tggtggtggt ggtggtgctc gagaccacct ctgagacgga    180
ggaccaggtg cagggtggac tctttctgga tgttgtagtc agacagggtg cgtccatctt    240
ccagctgttt cccagcaaag atcaacctct gctggtcagg agggatgcct tccttgtctt    300
ggatctttgc cttgacattc tcaatggtgt cactcggctc cacttcgaga gtgatggtct    360
taccagtcag ggtcttcacg aagatctgca tatgtatatc tccttcttaa agttaaacaa    420
aattatttct agagggaaac cgttgtggtc tccctatagt gagtcgtatt aatttcgcgg    480
gatcgagatc tcgggcagcg ttgggtcctg gccacgggtg cgcatgatcg tgctcctgtc    540
gttgaggacc cggctaggct ggcggggttg ccttactggt tagcagaatg aatcaccgat    600
acgcgagcga acgtgaagcg actgctgctg caaaacgtct gcgacctgag caacaacatg    660
aatggtcttc ggtttccgtg tttcgtaaag tctggaaacg cggaagtcag cgccctgcac    720
cattatgttc cggatctgca tcgcaggatg ctgctggcta ccctgtggaa cacctacatc    780
tgtattaacg aagcgctggc attgacccta gtgattttt ctctggtccc gccgcatcca    840
taccgccagt tgtttaccct cacaacgttc cagtaaccgg gcatgttcat catcagtaac    900
ccgtatcgtg agcatcctct ctcgtttcat cggtatcatt accccatga acagaaatcc    960 cccttacacg gaggcatcag tgaccaaaca ggaaaaaacc gcccttaaca tggcccgctt   1020
tatcagaagc cagacattaa cgcttctgga gaaactcaac gagctggacg cggatgaaca   1080
ggcagacatc tgtgaatcgc ttcacgacca cgctgatgag ctttaccgca gctgcctcgc   1140
gcgtttcggt gatgacggtg aaaacctctg acacatgcag ctcccggaga cggtcacagc   1200
ttgtctgtaa gcggatgccg ggagcagaca gcccgtcag ggcgcgtcag cgggtgttgg   1260
cgggtgtcgg ggcgcagcca tgacccagtc acgtagcgat agcggagtgt atactggctt   1320
aactatgcgg catcagagca gattgtactg agagtgcacc atatatgcgg tgtgaaatac   1380
cgcacagatg cgtaaggaga aataccgca tcaggcgctc ttccgcttcc tcgctcactg   1440
actcgctgcg ctcggtcgtt cggctgcggc gagcggtatc agctcactca aaggcggtaa   1500
tacggttatc cacagaatca ggggataacg caggaaagaa catgtgagca aaaggccagc   1560
aaaaggccag gaaccgtaaa aaggccgcgt tgctggcgtt tttccatagg ctccgccccc   1620
ctgacgagca tcacaaaaat cgacgctcaa gtcagaggtg gcgaaacccg acaggactat   1680
aaagatacca ggcgtttccc cctggaagct ccctcgtgcg ctctcctgtt ccgaccctgc   1740
cgcttaccgg atacctgtcc gcctttctcc cttcgggaag cgtggcgctt tctcatagct   1800
cacgctgtag gtatctcagt tcggtgtagg tcgttcgctc caagctgggc tgtgtgcacg   1860
```

-continued

```
aaccccccgt tcagcccgac cgctgcgcct tatccggtaa ctatcgtctt gagtccaacc    1920
cggtaagaca cgacttatcg ccactggcag cagccactgg taacaggatt agcagagcga    1980
ggtatgtagg cggtgctaca gagttcttga agtggtggcc taactacggc tacactagaa    2040
ggacagtatt tggtatctgc gctctgctga agccagttac cttcggaaaa agagttggta    2100
gctcttgatc cggcaaacaa accaccgctg gtagcggtgg ttttttttgtt tgcaagcagc   2160
agattacgcg cagaaaaaaa ggatctcaag aagatccttt gatcttttct acggggtctg    2220
acgctcagtg gaacgaaaac tcacgttaag ggattttggt catgagatta tcaaaaagga    2280
tcttcaccta gatcctttta aattaaaaat gaagttttaa atcaatctaa agtatatatg    2340
agtaaacttg gtctgacagt taccaatgct taatcagtga ggcacctatc tcagcgatct    2400
gtctatttcg ttcatccata gttgcctgac tccccgtcgt gtagataact acgatacggg    2460
agggcttacc atctggcccc agtgctgcaa tgataccgcg agacccacgc tcaccggctc    2520
cagatttatc agcaataaac cagccagccg aagggccga gcgcagaagt ggtcctgcaa     2580
ctttatccgc ctccatccag tctattaatt gttgccggga agctagagta agtagttcgc    2640
cagttaatag tttgcgcaac gttgttgcca ttgctgcagg catcgtggtg tcacgctcgt    2700
cgtttggtat ggcttcattc agctccggtt cccaacgatc aaggcgagtt acatgatccc    2760
ccatgttgtg caaaaaagcg gttagctcct tcggtcctcc gatcgttgtc agaagtaagt    2820
tggccgcagt gttatcactc atggttatgg cagcactgca taattctctt actgtcatgc    2880
catccgtaag atgcttttct gtgactggtg agtactcaac caagtcattc tgagaatagt    2940
gtatgcggcg accgagttgc tcttgcccgg cgtcaatacg ggataatacc gcgccacata    3000
gcagaacttt aaaagtgctc atcattggaa aacgttcttc ggggcgaaaa ctctcaagga    3060
tcttaccgct gttgagatcc agttcgatgt aacccactcg tgcacccaac tgatcttcag    3120
catcttttac tttcaccagc gtttctgggt gagcaaaaac aggaaggcaa aatgccgcaa    3180
aaaagggaat aagggcgaca cggaaatgtt gaatactcat actcttcctt tttcaatatt    3240
attgaagcat ttatcagggt tattgtctca tgagcggata catatttgaa tgtatttaga    3300
aaaataaaca aataggggtt ccgcgcacat ttccccgaaa agtgccacct gaaattgtaa    3360
acgttaatat tttgttaaaa ttcgcgttaa attttttgtta aatcagctca ttttttaacc    3420
aataggccga atcggcaaa atcccttata aatcaaaga atagaccgag atagggttga     3480
gtgttgttcc agtttggaac aagagtccac tattaaagaa cgtggactcc aacgtcaaag    3540
ggcgaaaaac cgtctatcag ggcgatggcc cactacgtga accatcaccc taatcaagtt    3600
ttttggggtc gaggtgccgt aaagcactaa atcggaaccc taaagggagc ccccgattta    3660
gagcttgacg gggaaagccg gcgaacgtgg cgagaaagga agggaagaaa gcgaaaggag    3720
cgggcgctag ggcgctggca agtgtagcgg tcacgctgcg cgtaaccacc acacccgccg    3780
cgcttaatgc gccgctacag ggcgcgtccc attcgcca                            3818
```

METHOD OF PURIFYING NATIVE UBIQUITIN

CROSS-REFERENCE TO RELATED APPLICATION

This application claims priority to and the benefit of Korean Patent Application No. 10-2019-0179913, filed on Dec. 31, 2019, the disclosure of which is incorporated herein by reference in its entirety.

BACKGROUND

1. Field of the Invention

The present invention relates to a method of purifying high-purity ubiquitin without acid or heat treatment.

2. Discussion of Related Art

Inside cells, protein homeostasis is maintained through the regulation of protein synthesis and degradation. Protein degradation is the breakdown process of proteins into short polypeptides or amino acids. As each protein has an unique half-life, a degradation rate, cell requires elaborate system to select proteins for degradation. Protein degradation pathways are divided into lysosome-mediated degradation and proteasome-mediated degradation. The lysosomal pathway collects proteins in lysosome to break down the proteins at once, and total 10 to 20% of proteins are degraded through this pathway. Whereas, most (80%) of intracellular proteins in the cytosol and the nucleus are degraded by the proteasome, after being labeled with ubiquitin (Ub). This ubiquitin mediated degradation process is called as the ubiquitin-proteasome system (UPS).

Ubiquitin is a small signaling protein, which consists of 76 amino acids. Ubiquitin is present in most of eukaryotic organisms, and it is found by Goldstein and his research team in 1975. A series of enzymes (E1, E2 and E3) support ATP-dependent ubiquitination process, in which ubiquitin is conjugated on a protein, and then the ubiquitinated protein is selectively degraded by the 26S proteasome complex. The ubiquitin-proteasome pathway includes two major steps, which occur in succession. The first step is covalent labeling of a substrate with multiple ubiquitin molecules, and the second step is degradation of the ubiquitin-labeled protein by the 26S proteasome complex. Although the major role of ubiquitin is a degradation of a protein, ubiquitin achieve numerous functions using its linkage types, including the regulation of enzyme activity, DNA repair, endocytosis, the regulation of gene expression and protein targeting. Also, malfunctioning of the ubiquitin system becomes a direct or indirect cause of various human diseases. Therefore, it is no exaggeration to say that an ubiquitin system (Ub system) orchestrates most of intracellular functions and ubiquitin is one of the key signaling molecules inside the cells.

Conventionally, ubiquitin has been purified from cells, using its acid-resistant or heat-resistant characteristic (Prep Biochem. 1985; 15(1-2):49-60.). In detail, most proteins are denatured and precipitated by treating an acid, such as perchloric acid and trichloric acid, or by boiling at 85° C. or higher temperature. On the other hand, proteins which endure such harsh conditions are remained in a supernatant. In this manner, ubiquitin is able to be obtained from the supernatant. However, these conventional methods cannot exclude a possibility to contaminate other acid-resistant or heat-resistant proteins. Hence, the purity of ubiquitin is restricted. Additionally, ubiquitin might be affected or denatured by acid or heat treatment, though it has been reported that ubiquitin is resistant to acids and heat.

In other point of view, ubiquitin might be purified by attaching an affinity tag and a protease cleavage site to ubiquitin. Affinity tag-based protein purification is universal method for protein purification. By inserting a protease cleavage site between the tag and the target protein, the tag is removed by an enzyme such as TEV protease. But this method has a disadvantage of leaving the remnants of a protease cleavage site in the target protein. For this reason, it is difficult to use this method for ubiquitin purification where both N-terminus and C-terminus of the target protein should be retained natively.

Accordingly, there is a need for an effective ubiquitin purification technique, which can overcome the limitations of the conventional method and obtain high-purity native ubiquitin.

SUMMARY OF THE INVENTION

As a result of earnest attempts to overcome the limitations of the conventional art, the inventors confirmed that high-purity ubiquitin is able to be obtained by linking only an affinity tag to the C-terminus of the ubiquitin and purifying it without additional protease cleavage site and acid or heat treatment. Finally, the present invention was completed.

Accordingly, the present invention is directed to provide a method for high-purity ubiquitin purification.

However, technical problems to be solved in the present invention are not restricted to the above-described problems, and other problems which are not described herein will be fully understood by the following description.

To achieve the object of the present invention, the present invention provides a method of purifying high-purity ubiquitin, which includes the following steps:

(a) introducing a vector expressing affinity tag-linked ubiquitin to a strain and culturing the strain;

(b) inducing expression of the protein in the cultured strain, harvesting and lysing the strain;

(c) performing affinity tag-based first purification using the lysate obtained in Step (b);

(d) dialyzing the first purified product and separating the affinity tag from the ubiquitin;

(e) performing second purification through chromatography using the dialyzed product obtained in Step (d); and (f) obtaining only a fraction containing the ubiquitin from the second purified product and concentrating the protein.

In one embodiment of the present invention, the affinity tag may be 2 to 10 histidine residues.

In another embodiment of the present invention, the strain may be *Escherichia coli* (*E. coli*).

In still another embodiment of the present invention, the *E. coli* may be a BL21(DE3) strain.

In yet another embodiment of the present invention, the vector may be pET23a-Ub-His6 (SEQ ID NO:1).

In yet another embodiment of the present invention, in Step (c), the first purification may be performed using Ni-NTA binding to the affinity tag.

In yet another embodiment of the present invention, in Step (d), the affinity tag is separated by treatment with a deubiquitinating enzyme.

In yet another embodiment of the present invention, the deubiquitinating enzyme may be USP2-cc.

In yet another embodiment of the present invention, in Step (e), the chromatography may be gel filtration chromatography.

In yet another embodiment of the present invention, the chromatography may be performed using a HiLoad 16/600 Superdex 200 prep grade column.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a diagram illustrating a method of purifying ubiquitin according to the present invention step by step;

DETAILED DESCRIPTION OF EXEMPLARY EMBODIMENTS

Figure 2A:
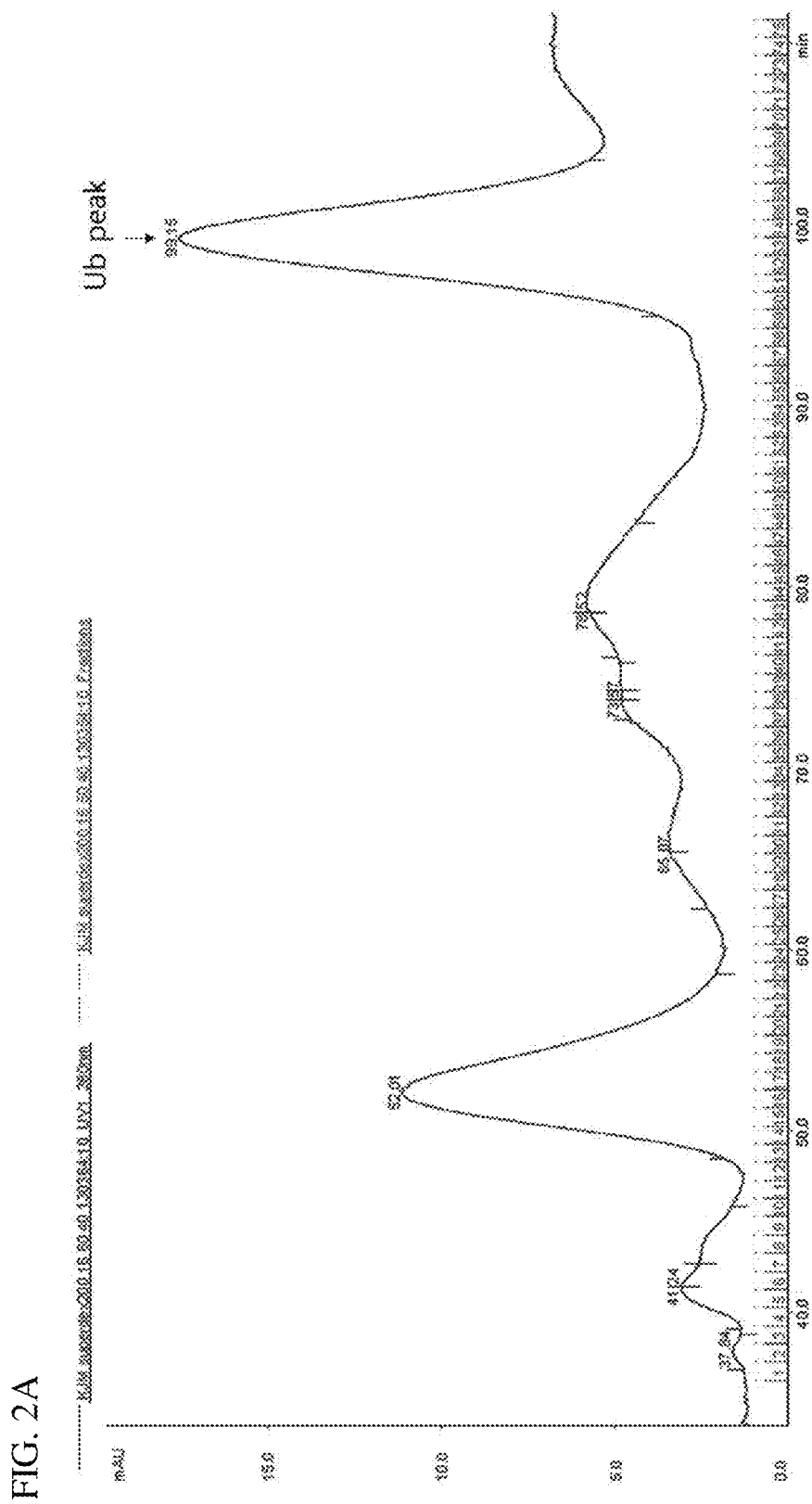
FIG. 2A shows a result of second purification through gel filtration chromatography after a tag was removed from a first purified product using a deubiquitinating enzyme.

The conventional ubiquitin purification method has taken advantage of a characteristic of ubiquitin being resistant to acids and heat. However, this method has limitations because of the possibility of mixing ubiquitin with other proteins resistant to an acid or heat, and the possibility of denaturing ubiquitin by acid or heat treatment. Accordingly, the inventors developed a method of purifying high-purity ubiquitin without acid or heat treatment, and thus the present invention was completed.

Therefore, a method of purifying high-purity ubiquitin, which includes the following steps, is provided:

(a) introducing a vector expressing an affinity tag-linked ubiquitin to a strain and culturing the strain;

(b) inducing expression of the protein in the cultured strain, harvesting and lysing the strain;

(c) performing affinity tag-based first purification using the lysate obtained in Step (b);

(d) dialyzing the first purified product and separating the affinity tag from the ubiquitin;

(e) performing second purification through chromatography using the product obtained in Step (d); and (f) obtaining only a fraction containing the ubiquitin from the second purified product and concentrating the ubiquitin.

The inventors performed above-described steps and confirmed the purification of the high-purity ubiquitin by performing CBB staining and western blotting through a specific example (see Example 1).

The term "purification" used herein refers to an operation of increasing purity by removing impurities mixed in a material, and may be accomplished by various methods such as recrystallization or fractional crystallization using a solubility difference, distillation or fractional distillation based on vapor pressure, partition/adsorption/ion exchange chromatography, and electrophoresis and gel filtration. In the present invention, it refers to an operation for obtaining a high-purity ubiquitin.

The term "high purity" used herein refers to a high proportion of a pure material, which is the main component. High purity in the present invention means that the proportion of ubiquitin is 80% or more, preferably 90% or more, more preferably 95% or more, still more preferably 98% or more, and most preferably 99% or more in the final product obtained through purification.

The protocol of the method of purifying high-purity ubiquitin according to the present invention is shown in FIG. 1, and the ubiquitin purification method will be described below step by step.

In the present invention, Step (a) is a process of transforming a strain to express an affinity tag-linked ubiquitin.

The strain is E. coli which is widely used to express a specific protein in the corresponding art, and preferably a BL21(DE3) strain, but the present invention is not limited thereto. The strain may be suitably selected by those of ordinary skill in the art.

The affinity tag may be histidine residues, preferably a string of 2 to 10 histidine residues, more preferably a string of 3 to 8 histidine residues, and still more preferably a string of 6 histidine residues, but the present invention is not limited thereto. The affinity tag may be suitably selected by those of ordinary skill in the art.

The vector is for expressing the ubiquitin with affinity tag, and the tag is linked to the C-terminus of the ubiquitin. Preferably, a pet23a-Ub-His6 vector (SEQ ID NO:1) is used, but the present invention is not limited thereto.

When the affinity tagged ubiquitin is expressed, it is possible to link one or more ubiquitin with the affinity tag, and a series of ubiquitin are separated in subsequent deubiquitination process.

In Step (a), the method of introducing a vector into a strain and the method of culturing the vector-introduced strain may be performed by methods conventionally used in the corresponding art.

In the present invention, Step (b) is for expressing an affinity tag-linked ubiquitin in the cultured strain, and obtaining a cell lysate containing the expressed protein.

The induction of expression of the affinity tag-linked ubiquitin may be achieved by treating the strain with isopropyl β-D-1-thiogalactopyranoside (IPTG). Induction condition is able to be adapted from conventionally known method in the corresponding art and the condition includes a treatment concentration, a culture temperature and culture time after treatment. Preferably, the induction is achieved through treatment of 0.5 mmol of IPTG and culture at 18° C. for 18 hours.

The IPTG is a compound widely used in the corresponding art to induce the expression of a specific protein in E. coli. Specifically, the IPTG is a similar molecule with allolactose, and initiates transcription of the lac operon such that the protein expression is induced when a gene encoding a specific protein is under the control of the lac operon.

In the present invention, Step (c) is for primarily purifying ubiquitin from the cell lysate obtained in Step (b).

The first purification step may be performed using a material recognizing and binding to an affinity tag on the ubiquitin, and in the present invention, the purification step may be performed using a binding between a histidine tag and Ni-NTA.

The Ni-NTA is a histidine tag-binding resin, and more specifically, $Ni^{2+}$-charged agarose is used to purify a recombinant protein having a polyhistidine (6×His) sequence. The purification step using the Ni-NTA may be suitably performed by those of ordinary skill in the art according to a conventional method used in the corresponding art.

In the present invention, Step (d) is for separating an affinity tag from the ubiquitin obtained through the first purification step in Step (c).

The step of separating an affinity tag from the ubiquitin may be achieved by treating a deubiquitinating enzyme. The deubiquitinating enzyme may be selected from the group consisting of USP2-cc, USP4, USP7 and USP25, and preferably, USP2-cc, but any enzyme having a function capable of separating the tag from the ubiquitin may be used without particular limitation.

The treatment with USP2-cc, which is a deubiquitinating enzyme, may be performed at 25 to 35° C. for 1 to 5 hours, preferably at 28 to 32° C. for 1 to 3 hours, and most preferably at 30° C. for 2 hours, but the present invention is not limited thereto.

With respect to the affinity tag-linked ubiquitin, the USP2-cc enzyme may be treated at a molar ratio of 1:0.001 to 1:0.1, preferably 1:0.005 to 0.05, and most preferably 1:0.01, but the present invention is not limited thereto.

In the present invention, Step (e) is for purifying ubiquitin from the separated affinity tag and the deubiquitinating enzyme through chromatography performed on the purified product obtained in Step (d) and increasing the purity of ubiquitin.

For the chromatography, any method that can separate a deubiquitinating enzyme from ubiquitin may be selected from various types of methods known in the corresponding art without particular limitation, and preferably, gel filtration chromatography is used.

The gel filtration chromatography is a type of liquid chromatography, which uses a difference in retention time according to the size and shape of a solute molecule, and more specifically, uses the principle in which solute molecules infiltrate into a fine pore of packing particles and smaller particles contacting a solid for a long time is separated from larger particles not moving into the pore and contacting a solid only for a short time. A column used in the chromatography may be suitably selected according to a material to be separated, and specifically, selected from Superdex 200 prep grade, Superdex 75 prep grade, Superdex 200 increase, Superdex 75 increase, Superose 12 prep grade and Superose 6 prep grade. The column is preferably a HiLoad 16/600 Superdex 200 prep grade column, but the present invention is not limited thereto.

In the present invention, Step (f) is for obtaining high-concentration ubiquitin by concentrating the ubiquitin fraction obtained through the chromatography.

The ubiquitin fraction may be separated by confirming a UV 280-nm peak pattern through the chromatography with the obtained product, and in the embodiment of the present invention, FIG. 2A shows a clear Ubiquitin peak. Through this manner, only the fraction containing ubiquitin may be collected.

A method of concentrating the ubiquitin fraction may be performed using a conventionally used material, and in the present invention, a commercially available Vivaspin 15R tube was used as a filtering apparatus for purification and/or concentration of a biological sample, but the present invention is not limited thereto.

Figure 2B:
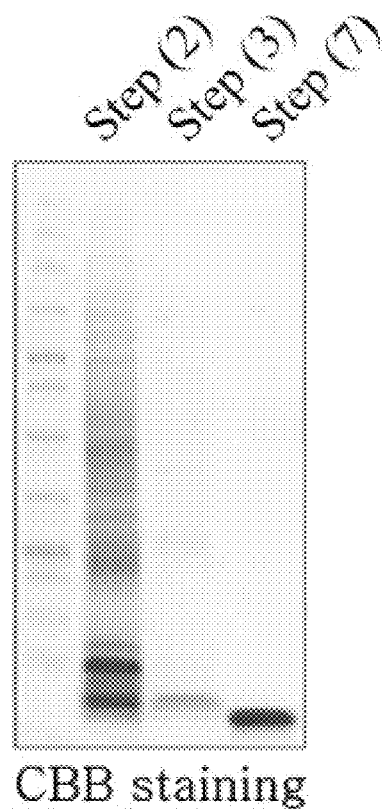
FIG. 2B shows purities of the purified ubiquitin by performing SDS-PAGE (Sodium dodecyl sulfate-polyacrylamide gel electrophoresis) and CBB (Coomassie Brilliant Blue) staining. Each lane indicates a lysate extracted from E. coli BL21 (DE3) strain expressing affinity tag-linked ubiquitin (Step (2) in examples), an intermediate product obtained by affinity tag-based first purification using lysate from Step (2) (Step (3) in examples), and a final product of the purified ubiquitin (Step (7) in examples)
Figure 2C:
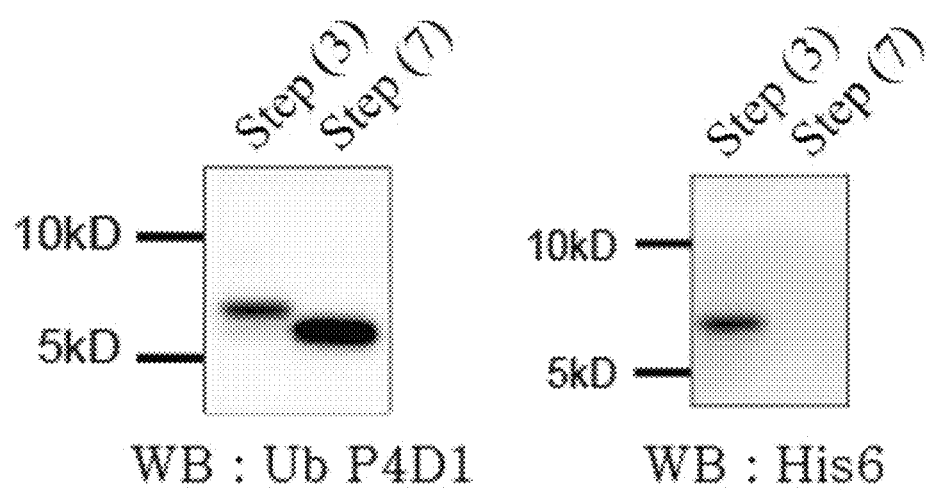
FIG. 2C shows the western blotting performed on the purified products obtained in Steps (3) and (7) using a ubiquitin-specific antibody (Ub P4D1) and an affinity tag-specific antibody (His6), respectively.

In the embodiment of the present invention, the purified product finally obtained as described above was subjected to CBB and western blotting, and as shown in FIGS. 2B and 2C, it was confirmed that a high-purity ubiquitin is separated without impurities, comparing the first purified product obtained in Step (c) (Step (3) in Examples) with the final purified product (Step (7) in Examples).

Hereinafter, to help in understanding the present invention, practical examples will be suggested. However, the following examples are merely provided to help understanding of the present invention, and not to limit the present invention.

EXAMPLES

Example 1. Purification of Ubiquitin

The inventors designed a method of purifying the ubiquitin using an affinity tag and a deubiquitinating enzyme without acid or heat treatment which has been conventionally used as a method of purifying the ubiquitin.

More specifically, high-purity ubiquitin was obtained by performing purification according to the following steps: First, pET23a-Ub-His6 vector (SEQ ID NO: 1) expressing the ubiquitin (Ub-His6) to which His6 was linked as an affinity tag was transformed into an *E. coli* BL21(DE3) (Step (1)). The transformed strain was cultured in 250 mL LB media, treated with 0.5 mmol of isopropyl β-D-1-thiogalactopyranoside (IPTG), and cultured at 18° C. for 18 hours to induce expression of Ub-His6 proteins in the strain, and the strain was recovered and lysed, thereby obtaining a lysate (Step (2)). Subsequently, using the lysate obtained as described above, the Ub-His6 protein was primarily purified using Ni-NTA (Step (3)). The Ub-His6 protein purified through the primary purification was then dialyzed and reacted with USP2-cc (Molar ratio of Ub-His6:USP2-cc=100:1), which is one of the deubiquitinating enzymes, for 2 hour at 30° C. to separate the His6 tag from the ubiquitin (Step (4)). Afterward, second purification was performed on the His6 tag-separated ubiquitin through gel filtration chromatography using a HiLoad 16/600 Superdex 200 prep grade column (Step (5)). By confirming a UV peak pattern at 280 nm after chromatography, as shown in FIG. 2A, a separated peak of the ubiquitin fraction is confirmed. Finally, a high-purity ubiquitin was obtained by collecting only the fraction (Step (6)) and concentrating the fraction using a VIVASPIN R15 tube (Step (7)).

As a result of performing sodium dodecyl sulfate-polyacrylamide gel electrophoresis (SDS-PAGE) using the eluate obtained in Step (2) and the purified products obtained in Steps (3) and (7), respectively, and staining them with Coomassie Brilliant Blue (CBB), as shown in FIG. 2B, the His-tagged ubiquitin was purified through the first purification in Step (3), and it was confirmed that the native ubiquitin was highly purified without impurities in Step (7).

In addition, from the western blotting result shown on the left side of FIG. 2C, the purified product obtained in Step (7) has a smaller protein size compared to Step (3), confirming that the ubiquitin was separated with the affinity tag and then highly concentrated. From the western blotting result using His6-specific antibodies, shown on the right side of FIG. 2C, it was confirmed that His6 was completely removed from the ubiquitin comparing the products obtained in Step (3) and Step (7), through deubiquitination.

A method of purifying ubiquitin according to the present invention, compared to a conventional purification method using acid or heat treatment, can overcome limitations of mixing other proteins resistant to acids or heat or denaturing the ubiquitin and purify high-purity ubiquitin, and the ubiquitin obtained thereby can be effectively used for various purposes in the corresponding art.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

What is claimed is:

1. A method of purifying native ubiquitin without acid or heat treatment, comprising the following steps:
   (a) introducing a vector expressing an affinity tag-linked ubiquitin to a strain and culturing the strain, wherein the vector comprises SEQ ID NO:1 (pET23a-Ub-His6);
   (b) inducing expression of the protein in the cultured strain, harvesting and lysing the strain;
   (c) performing a first purification which is an affinity tag-based first purification using the lysate obtained in Step (b);
   (d) dialyzing the product of the first purification step and separating the affinity tag from the ubiquitin;
   (e) performing a second purification through chromatography using the product obtained in Step (d); and
   (f) obtaining a solution comprising ubiquitin from the chromatographic purification, wherein the affinity tag is linked to the C-terminus of the ubiquitin.

2. The method of claim 1, wherein the affinity tag is 2 to 10 histidine residues.

3. The method of claim 1, wherein the strain is *Escherichia coli*.

4. The method of claim 3, wherein the *Escherichia coli* is a BL21 (DE3) strain.

5. The method of claim 1, wherein the first purification is performed using Ni-NTA binding to the affinity tag in Step (c).

6. The method of claim 1, wherein the affinity tag is separated by treatment with a deubiquitinating enzyme in Step (d).

7. The method of claim 6, wherein the deubiquitinating enzyme is ubiquitin specific peptidase 2 catalytic core (USP2-cc).

8. The method of claim 1, wherein the chromatography is gel filtration chromatography in Step (e).

9. The method of claim 8, wherein the chromatography is performed using a HiLoad 16/600 Superdex 200 prep grade column.

* * * * *